United States Patent [19]

Sabatelli

[11] Patent Number: 4,822,602
[45] Date of Patent: Apr. 18, 1989

[54] COSMETIC STICKS

[75] Inventor: Anthony D. Sabatelli, Hamilton, Ohio

[73] Assignee: The Procter & Gamble Company, Cincinnati, Ohio

[21] Appl. No.: 43,909

[22] Filed: Apr. 29, 1987

[51] Int. Cl.$^4$ .......................... A61K 7/32; A61K 7/34; A61K 7/36; A61K 7/38

[52] U.S. Cl. .............................. 424/65; 424/DIG. 5; 424/66; 424/67; 424/68

[58] Field of Search ...................... 424/65, 68, DIG. 5

[56] References Cited

U.S. PATENT DOCUMENTS

| | | | |
|---|---|---|---|
| 2,732,327 | 1/1956 | Teller | 424/65 |
| 2,857,315 | 10/1958 | Teller | 424/65 |
| 2,900,306 | 8/1959 | Slater | 424/65 |
| 2,970,083 | 1/1961 | Bell | 424/65 |
| 4,120,948 | 10/1978 | Shelton | 424/66 |
| 4,122,029 | 10/1978 | Gee et al. | 252/309 |
| 4,126,679 | 11/1978 | Davy et al. | 424/66 |
| 4,202,879 | 5/1980 | Shelton | 424/66 |
| 4,226,889 | 10/1980 | Yuhas | 424/DIG. 5 |
| 4,229,432 | 10/1980 | Geria | 424/DIG. 5 |
| 4,265,878 | 5/1981 | Keil | 424/68 |
| 4,268,498 | 5/1981 | Gedeon et al. | 424/DIG. 5 |
| 4,322,400 | 3/1982 | Yuhas | 424/DIG. 5 |
| 4,382,079 | 5/1983 | Marschner | 424/65 |
| 4,440,741 | 4/1984 | Marschner | 424/65 |
| 4,440,742 | 4/1984 | Marschner | 424/65 |

Primary Examiner—Dale R. Ore
Attorney, Agent, or Firm—Kim William Zerby; Steven J. Goldstein; Richard C. Witte

[57] ABSTRACT

The present invention relates to cosmetic compositions in the form of solid sticks, especially deodorant sticks and antiperspirant sticks. The cosmetic stick compositions of the present invention comprise the essential components: (a) water-soluble active; (b) dimethicone copolyol; (c) volatile silicone oil; (d) propylene glycol; (e) $C_2$-$C_4$ monohydric alcohol; (f) water; (g) solidifying agent; and (h) coupling agent. These compositions have excellent efficacy and cosmetic aesthetics.

The present invention also relates to methods for treating or preventing malodor associated with human perspiration, especially underarm odor. The present invention further relates to methods for manufacturing cosmetic stick compositions of the present invention.

17 Claims, No Drawings

COSMETIC STICKS

BACKGROUND OF THE INVENTION

The present invention relates to cosmetic compositions in the form of solid sticks, especially deodorants sticks and antiperspirant sticks. These compositions have excellent efficacy and cosmetic aesthetics. The present invention further relates to methods for the treatment or prevention of malodor associated with human perspiration, especially underarm odor.

Attempts have been made to realize cosmetic sticks which deliver active ingredients to the skin, such as deodorant and/or antiperspirant materials. Cosmetically preferred sticks glide easily over the skin surface, are not perceived as feeling gritty, and do not leave a visible residue. Soaps/alcohol gels can provide some of such cosmetic benefits. Examples of such soap gels are disclosed in U.S. Pat. No. 2,732,327, to Teller, issued Jan. 24, 1956; U.S. Pat. No. 2,857,315, to Teller, issued Oct. 21, 1958; U.S. Pat. No.2,900,306, to Slater, issued Aug. 18, 1959; and U.S. Pat. No. 2,970,083, to Bell, issued Jan. 31, 1961. In addition, U.S. Pat. No. 4,382,742, to Marschner, issued Apr. 3, 1984 described aqueous, transparent sticks containing bicarbonate in a propylene glycol/metal stearate gel. Wax based bicarbonate sticks containing silicones are described in U.S. Pat. No. 4,126,679, to Davy et al., issued Nov. 21, 1978. Emulsion sticks are also well known, having been disclosed, for example, in U.S. Pat. No. 4,122,029, to Gee et al., issued Oct. 24, 1978, and U.S. Pat. No. 4,265,878, to Keil, issued May 5, 1981.

While cosmetic sticks are old as evidenced by certain of the above patents, none of these publications suggests the criticality of the specific combination of components described by the present invention. This combination of components gives cosmetic sticks which are both highly efficacious and cosmetically pleasing.

It is therefore an object of the present invention to provide cosmetic sticks which have excellent cosmetic properties (e.g., ease of application to skin, "glide", a lack of visible residue) and are easy to manufacture. A further object of the present invention is to provide cosmetic sticks which very effectively deliver water-soluble active materials, particularly deodorant and/or antiperspirant active materials, to the skin. A still further object of the present invention is to provide cosmetic compositions which feel dry; do not feel greasy or gritty; go on clean and clear; remain clear without no visible cakey, chalky residue after application; and appear semi-opaque, uniform, and non-gritty. An object of the present invention is also to provide methods for treating or preventing malodor associated with human perspiration, especially underarm odor.

It has been surprisingly discovered that the above objectives can be realized by formulating a stick comprising the ingredients described hereinafter.

All percentages and ratios used herein are by weight of the total composition unless otherwise designated.

SUMMARY OF THE INVENTION

The present invention relates to cosmetic stick compositions, especially cosmetic stick compositions useful as deodorants or antiperspirants, comprising:
(a) from about 0.1% to about 50% of at least one water-soluble active;
(b) from about 5% to about 25% of at least one dimethicone copolyol;
(c) from about 1% to about 25% of at least one volatile silicone oil;
(d) from about 5% to about 20% of propylene glycol;
(e) from about 1% to about 15% of at least one $C_2$-$C_4$ monohydric alcohol;
(f) from about 10% to about 50% water;
(g) from about 1% to about 25% of at least one solidifying agent; and
(h) from about 1% to about 30% of at least one coupling agent.

The present invention also relates to methods for treating or preventing malodor associated with human perspiration, especially underarm odor. These methods comprise applying to the skin of a human a safe and effective amount of a deodorant or antiperspirant cosmetic stick composition of the present invention.

The present invention further relates to methods for manufacturing cosmetic stick compositions of the present invention. These methods comprise the steps of: (a) dissolving at least one water-soluble active in an aqueous phase comprising the water component of the composition; followed by (b) mixing this aqueous active solution with an organic phase comprising at least one of the components of the composition selected from dimethicone copolyol, volatile silicone oil, or mixtures thereof.

DETAILED DESCRIPTION OF THE INVENTION

Cosmetic Stick Compositions

The cosmetic stick compositions of the present invention comprise the following components: (a) water-soluble active; (b) dimethicone copolyol; (c) volatile silicone oil; (d) propylene glycol; (e) $C_2$-$C_4$ monohydric alcohol; (f) water; (g) solidifying agent; and (h) coupling agent. The specific components to be included in the cosmetic sticks of the present invention, and their levels, are selected in order to produce a stick of desired hardness so as to maintain dimensional stability while depositing a suitable amount of the water-soluble active onto the skin during normal use. These components, and the weight percentages for these components, are described in detail immediately hereinafter.

(a) Water-Soluble Active

The compositions of the present invention essentially comprise at least one water-soluble active. The term "water-soluble active", as used herein, means any compound, composition, or combination thereof soluble in the aqueous phase of the compositions of the present invention and safe for topical application to human skin. The aqueous phase of the composition of the present invention includes both the water component and the monohydridic alcohol component, with the preferred water-soluble actives being soluble to the extent utilized in the composition in the amount of water being utilized in the composition. The water-soluble active components must be stable in the formulations of the instant invention.

Water-soluble actives may be, for example, anti-inflammatory agents, analgesic agents, suntanning agents, sunscreens, antibacterial agents, deodorant actives, antiperspirant actives, or mixtures thereof. Preferred water-soluble actives for use herein are deodorant actives, antiperspirant actives, or mixtures thereof. More preferred are deodorant actives.

Antiperspirant actives useful as water-soluble actives in the present invention are well known in the art, and are disclosed generally in Miller and Hoag, "Personal Care Products", *Handbook of Nonprescription Drugs*, 8th Edition, Chapter 19, pages 397–417 (American Pharmaceutical Association; 1986), the disclosures of which are incorporated herein by reference in their entirety. Antiperspirant actives include, for example, aluminum chlorohydrates, aluminum chloride, sodium aluminum chlorohydroxy lactate, buffered aluminum sulfate, and aluminum zirconium chlorohydrates. Astringent metallic salts are preferred antiperspirant actives, and may be incorporated in the instant compositions at levels from about 10% to about 50%, preferably from about 10% to about 40%, and more preferably from about 15% to about 30%.

Preferred astringent metallic salts include the inorganic and organic salts of aluminum, zirconium and zinc, and mixtures thereof. Particularly preferred are the aluminum and zirconium salts, such as aluminum halides, aluminum hydroxyhalides zirconyl oxyhalides, zirconyl hydroxyhalides, and mixtures thereof. Such metal salts, and complexes thereof, are described in European Patent Specification Publication No. 117,070, to May, published Aug. 29, 1984, and U.S. Pat. No. 4,137,306, to Rubino et al., issued Jan. 30, 1979, and disclosures of both these patent specifications being incorporated herein by reference in their entirety.

Preferred aluminum salts include those of the formula:

$$Al_2(OH)_a Cl_b \cdot xH_2O$$

wherein a is from about 2 to about 5; $a+b=6$; x is from about 1 to about 6; and wherein a, b, and x may have non-integer values. Particularly preferred are aluminum chlorhydroxides referred to as "5/6 basic chlorhydroxide", wherein $a=5$; and "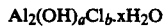 basic chlorhydroxide", wherein $a=4$. Processes for preparing aluminum salts are disclosed in the following documents, all incorporated by reference herein in their entirety; U.S. Pat. No. 3,887,692, to Gilman, issued June 3, 1975; U.S. Pat. No. 3,904,741, to Jones et al., issued Sept. 9, 1975; U.S. Pat. No. 4,359,456, to Gosling et al., issued Nov. 16, 1982; and British Patent Specification No. 2,048,229, to Fitzgerald et al., published Dec. 10, 1980. Mixtures of aluminum salts are described in British Patent Specification No. 1,347,050, to Shin et al., published Feb. 27, 1974, the disclosures of which are incorporated herein by reference in their entirety.

Zirconium salts are also preferred for use in antiperspirant sticks in the present invention. Such salts are of the general formula:

$$ZrO(OH)_{2-a}Cl_a \cdot xH_2O$$

wherein a is from about 1 to about 2, preferably from about 1.5 to about 1.87; x is from about 1 to about 7; and wherein a and x may have non-integer values. These zirconium salts are disclosed in Belgium Patent Specification 825,146, to Schmitz, issued Aug. 4, 1975, the disclosures of which are incorporated herein by reference in their entirety. Particularly preferred zirconium salts are those complexes also containing aluminum and glycine, commonly known as "ZAG complexes". Such ZAG complexes contain aluminum chlorhydroxide and zirconyl hydroxychloride of the formulae detailed above. These compounds in ZAG complexes are disclosed in the following patent documents, all incorporated by reference herein in their entirety; U.S. Pat. NO. 2,814,585, to Daley, issued Nov. 26, 1957; U.S. Pat. No. 3,679,068, to Luedders et al., issued Feb. 12, 1974; U.S. Pat. No. 4,017,599, to Rubino, issued Apr. 12, 1977; U.S. Pat. No. 4,120,948, to Shelton, issued Oct. 17, 1978; and British Patent Specification No. 2,144,992, to Callaghan et al., published Mar. 20, 1985.

Deodorant actives useful as water-soluble actives in the present invention are also well known in the art. These actives have been disclosed in Miller and Hoag, "Personal Care Products", *Handbook of Nonperscription Drugs*, 8th Edition, Chapter 19, pages 397–417 (American Pharmaceutical Association; 1986), the disclosures of which are incorporated by reference herein in their entirety. These deodorant actives are typically bactericides, fungicides, or mixtures thereof. Such deodorant actives are usually present at levels of from about 0.1% to about 10%, preferably from about 1% to about 10%, by weight of the composition. Suitable deodorant actives include bacteriostatic quaternary ammonium compounds such as cetyl-trimethyl ammonium bromide, cetyl pyridinium chloride, benzethonium chloride, diisobutylbenoxyethoxyethyldimethylbenzyl ammonium chloride, sodium N-lauryl sarcosine, sodium N-polymethyl sarcosine, lauroyl sarcosine, N-myristolyl glycine, potassium N-lauroyl sarcosine, steryl trimethyl ammonium chloride, and mixtures thereof. Other deodorant actives include carbonate salts and bicarbonate salts.

Preferred deodorant actives for use in the compositions of the present invention are carbonate and bicarbonate salts, and mixtures thereof, such as, for example, alkali metal carbonates, alkali metal bicarbonates, and ammonium and tetraalkylammonium carbonate and bicarbonate salts. More preferred are the alkali metal carbonates, and especially alkali metal bicarbonates, such as, for example, sodium carbonate, potassium carbonate, potassium bicarbonate, and especially sodium bicarbonate, or mixtures thereof. The carbonate and bicarbonate salts typically comprise in total from about 0.1% to about 10%, preferably from about 1% to about 10%, and most preferably from about 1% to about 6%, of the compositions herein.

The water-insoluble actives in total typically comprise from about 0.1% to about 50% by weight of the composition of the present invention, more preferably from about 1% to about 40%, and most preferably from about 1% to about 30%.

(b) Dimethicone Copolyol

Another essential component of the compositions of the present invention is at least one silicone-containing material referred to herein as "dimethicone copolyol" which is one or more polyalkylene oxide modified dimethylpolysiloxanes. The dimethicone copolyols include the polyalkylene oxide modified dimethylpolysiloxanes of the following formulae:

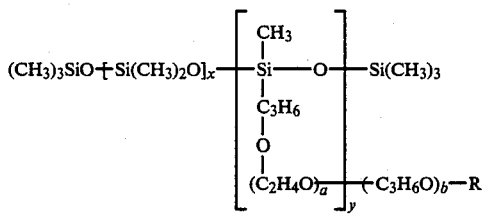

and

wherein R is hydrogen, an alkyl group having from about 1 to about 12 carbon atoms, an alkoxy group having from about 1 to about 6 carbon atoms, or a hydroxyl group; R' and R" are alkyl groups having from 1 to about 2 carbon atoms; x is an integer of from 1 to 100, preferably from 20 to 30; y is an integer of 1 to 20, preferably from 2 to 10; and a and b are integers of from 0 to 50, preferably from 20 to 30.

Dimethicone copolyls among those useful herein are disclosed in the following patent documents, all incorporated by reference herein in their entirety; U.S. Pat. No. 4,122,029, to Gee et al., issued Oct. 24, 1978; U.S. Pat. No. 4,265,878, to Keil, issued May 5, 1981; and U.S. Pat. No. 4,421,769, to Dixon et al., issued Dec. 20, 1983. Commercially available dimethicone copolyols, useful herein, include Silwet Surface Active Copolymers (manufactured by the Union Carbide Corp.), Dow Corning Silicone Surfactants (manufactured by the Dow Corning Corp.); Silicone Copolymer F-754 (manufactured by SWS Silicones Corp.); and Rhodorsil 70646 Fluid (manufactured by Rohne Poulenc, Inc.). Dow Corning 3225C Silicone Fluid is a preferred dimethicone copolyol.

The dimethicone copolyol typically comprises in total from about 5% to about 25%, preferably from about 10% to about 20%, and most preferably from about 12% to about 18%, of the compositions of the present invention.

(c) Volatile Silicone Oil

The compositions of the present invention also essentially comprise at least one volatile silicone oil at a level in total of from about 1% to about 25%, preferably from about 5% to about 15%, and most preferably from about 7% to about 13%. The term "volatile", as used herein, refers to those materials which have a measurable vapor pressure at ambient temperature and is not dimethicone copolyol.

The volatile silicone oils useful in the cosmetic stick compositions of the present invention are preferably cyclic or linear polydimethylsiloxanes containing from about 3 to about 9, preferably from about 4 to about 5, silicone atoms. The following formula illustrates the cyclic volatile polydimethylsiloxanes useful in the cosmetic stick compositions disclosed herein:

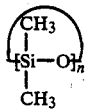

wherein n equals about 3 to about 7. The linear polydimethylsiloxanes contain from about 3 to about 9 silicone atoms per molecule and having the following general formula:

wherein n equals about 1 to about 7. The linear volatile silicone materials generally have viscosities of less than about 5 centistokes at 25° C. while the cyclic materials have viscosities of less than about 10 centistokes. A description of various volatile silicone oils is found in Todd, et al., "Volatile Silicone Fluids for Cosmetics", *Cosmetics & Toiletries*, 91, pages 27–32 (1976), the disclosures of which is incorporated by reference herein in their entirety.

Examples of the preferred volatile silicone oils useful herein include: Dow Corning 344, Dowing Corning 345, and Dow Corning 200 (manufactured by the Dow Coring Corp.); Silicone 7207 and Silicone 7158 (manufactured by the Union Carbide Corp.); SF 1202 (manufactured by General Electric); and SWS-03314 (manufactured by SWS Silicones, Inc.).

(d) Propylene Glycol

Another essential component of the present invention is propylene glycol. The propylene glycol comprises from about 5% to about 20%, more preferably from about 7% to about 17%, and most preferably from about 10% to about 15%, of the compositions of the present invention.

(e) $C_2$–$C_4$ Monohydric Alcohol

The compositions of the present invention further essentially comprise at least one $C_2$–$C_4$ monohydric alcohol. Preferred monohydric alcohols are selected from the group consisting of ethanol, n-propanol, iso-propanol, n-butanol, iso-butanol, sec-butanol, tert-butanol, and mixtures thereof. More preferred are ethanol, n-propanol, iso-propanol, and mixtures thereof. Most preferred is ethanol.

The $C_2$–$C_4$ monohydric alcohols comprise in total from about 1% to about 15%, preferably from about 3% to about 13%, and most preferably from about 5% to about 10%, of the compositions of the present invention.

(f) Water

A further essential component of the present invention is water. Water is typically present at a level of from about 10% to about 50%, preferably from about 10% to about 40%, and most preferably from about 15% to about 25%.

(g) Solidifying Agent

Another essential component of the compositions herein is at least one solidifying agent. As is appreciated by those skilled in the art, the selection of a particular solidifying agent will vary depending upon the particular type of cosmetic stick desired (e.g., wax stick; gel stick). A variety of solidifying agents among those useful herein, as well as stick vehicles made from these materials, are described in the following documents, all incorporated by reference herein in their entirety: Plechner, "Antiperspirants and Deodorants", *Cosmetics, Science and Technology*, 2, pages 373–416 (Balsam and Sagarin, editors; 1972); Fox "Gel and Sticks Review and Update", *Cosmetics & Toiletries*, 99, pages 19–52 (1984); Geria, "Formulation of Stick Antiperspirants and Deodorants", *Cosmetics & Toiletries*, 99, pages 55-99 (1984); and "Gels and Sticks Formulary", *Cosmetics & Toiletries*, 99, pages 77-87 (1984). Preferred solidifying agents are gel forming agents and especially soap type gel forming agents. The preferred solidifying agents which are soap type gel forming agents are sodium potassium, and aluminum salts of fatty acids containing from about 14 to about 18 carbon atoms.

Soap type gel forming agents generally comprise from about 1% to about 15%, preferably from about 3% to about 10%, and most preferably from about 3% to about 8%, of the composition. The fatty acid portion of the soap type gel forming agent should preferably be essentially pure saturated or unsaturated higher fatty acids having a $C_{14}$-$C_{18}$ backbone. Suitable mixtures of such acids can be employed provided that such mixtures are free from significant proportions of other fatty acids of higher or lower chain length which substantially adversely affect or neutralize the desired gel forming effects.

Examples of fatty acids useful in synthesizing the soap type gel forming agents herein include: myristic, palmitic, stearic, oleic, linoleic, linolenic, margaric, and mixtures of such acids. Naturally occurring sources of such fatty acids include coconut oil, beef tallow, lanolin, fish oil, beeswax, palm oil, peanut oil, olive oil, cottonseed oil, soybean oil, corn oil, rapeseed oil, rosin acids and grasses. Conventional fractionation and/or hydrolysis techniques can be employed if necessary to obtain the requisite types of fatty acids from such materials.

Preferred fatty acid soap type gel forming agents include: sodium stearate, sodium palmitate, potassium stearate, potassium palmitate, sodium myristate, and aluminum monostearate. Mixtures of soap type gel forming agents may also be used. The most preferred soap type gel forming agent is sodium stearate.

If an antiperspirant active is to be included in the gel type compositions of the present invention, it is preferred that the solidifying agent not be a soap type gel forming agent as described hereinbefore but rather a gel forming agent which is a benzylidene alcohol. Such materials are generally disclosed in British Patent Specification No. 1,291,819, published Oct. 4, 1972, the disclosures of which are incorporated by reference herein in their entirety. A preferred benzylidene sorbitol for use in the compositions of the present invention is dibenzylidene monosorbitol acetal (DBMSA). This material is commercially available, such as GELL-ALL-D (manufactured by New Japan Chemical Company, Ltd.) and MILLITHIX 925 (manufactured by Millikin Chemical, Division of Millikin & Company).

As is appreciated by those skilled in the art, certain of the antiperspirant compositions described above containing benzylidene sorbitol may need to be buffered in order to provide effective and/or stable cosmetic sticks of the present invention. Accordingly, such benzylidene sorbitol-containing antiperspirant sticks of this invention may also contain a buffering agent so as to maintain a pH of at least about 6.0 in the composition. Such buffering agents are described in U.S. Pat. No. 4,154,816, to Roehl et al., issued May 15 1975; U.S. Pat. No. 4,346,079, to Roehl et al., issued Aug. 24, 1982; and U.S. Pat. No. 4,518,582, to Schamper et al., issued May 21, 1985, the disclosures of all these patent specifications being incorporated herein by reference in their entirety.

Solidifying agents preferred for use in cosmetics sticks of the present invention containing antiperspirant actives are waxy materials typically incorporated at a level of from about 1% to about 25%, preferably from about 5% to about 25%. Among such waxy materials useful herein are the high melting point waxes, having a melting point of from about 65° C. to 102° C. Lower melting point waxes having a melting point of from about 37° C. to 75° C. are preferred. Such low-melting point waxes include fatty acids, fatty alcohols, fatty acid esters and fatty acid amides, and mixtures thereof. Solidifying agents among those useful in the wax type cosmetic sticks of this invention are disclosed in the following patent specifications, all of which are incorporated by reference herein in their entirety: U.S. Pat. No. 4,049,792, to Elsnau, issiued Sept. 20, 1977; U.S. Pat. No. 4,151,272, to Geary et al, issued Apr. 24, 1975; U.S. Pat. No. 4,229,432, to Geria, issued Oct. 21, 1980; U.S. Pat. No. 4,280,994, to Turney, issued July 28, 1981; U.S. Pat. No. 4,126,679, to Davy et al, issued Nov. 21, 1978; and European Patent Application Publication No. 117,070, to May, published Aug. 29, 1984.

The solidifying agent typically comprises from about 1% to about 25%, preferably from about 1% to about 15%, and more preferably from about 3;1% to about 10% by weight of the compositions of the present invention.

(h) Coupling Agents

The compositions of the present invention also essentially comprise at least one coupling agent. The term "coupling agent", as used herein, means any compound, composition, or combination thereof which acts to bring the polar and non-polar components of the present invention into a homogeneous cosmetic stick composition. Preferably the coupling agent is selected from the group consisting of $C_6$-$C_{22}$ fatty alcohols, ethoxylated derivatives of $C_4$-$C_{22}$ fatty alcohols, propoxylated derivatives of $C_4$-$C_{22}$ fatty alcohols, and mixtures thereof as described, for example, in *Drug & Cosmetic Industry*, 138 (2), p. 40 (1986), the disclosures of which are incorporated herein by reference in their entirety. More preferred coupling agents are ethoxylated derivatives of $C_{10}$-$C_{20}$ fatty alcohols, propoxylated derivatives of $C_{10}$-$C_{20}$ fatty alcohols, and mixtures thereof. The coupling agents to be used in the compositions of the present invention further most preferably have a Hydrophile-Lipophile Balance ("HLB") value within the range of from about 5 to about 18, preferably from from about 8 to about 15. The HLB value system is fully described, and values for various materials are provided, in the publication *The HLB System, A Time-Saving Guide to Emulsifier Selection* (published by ICI Americas Inc., Wilmington, Del.; 1984), the disclosures of this publication being incorporated by reference herein in its entirety.

More preferred coupling agents for use herein are polypropylene glycol ("PPG") ethers of $C_4$-$C_{22}$ (preferably $C_{10}$-$C_{20}$) fatty alcohols. Examples of such materials are: PPG-4 myristyl ether, PPG-4 lauryl ether, PPG-10 cetyl ether, PPG-3 myristyl ether, and mixtures thereof. Additional examples are found in *CTFA Cosmetic Ingredient Dictionary*, Third Edition (Estrin et al., Editors; The Cosmetic, Toiletry and Fragrance Association, Inc.; 1982), pages 252-260 and 494-500, the disclosures of which are incorporated herein by reference in their entirety. Most preferred are PPG-10 cetyl ether (HLB value calculated to be about 14.5), PPG-3 myristyl ether (HLB value calculated to be about 9.8), and especially mixtures thereof.

The coupling agents therefore typically comprise from about 1% to about 30%, preferably from about 5% to about 25%, and most preferably from about 15% to about 25%, of the compositions of the present invention. When the preferred PPG-10 cetyl ether and/or PPG-3 myristyl ether are present in the compositions of the present invention, it is preferred that each material individually comprise from about 0% to about 25% of the weight of the compositions such that their individual or combined weight comprises from about 15% to about 25% of the composition's weight. More preferred are mixtures of PPG-10 cetyl ether and PPG-3 myristyl ether comprising in total from about 15% to about 25% of the composition in weight ratios of PPG-10 cetyl ether: PPG-3 myristyl ether in the range of from about 19:1 to about 1:1, preferably from about 4:1 to about 1:1.

(i) Optional Components

The compositions of the present invention also preferably contain optional components which modify the physical characteristics of the cosmetic sticks. Such components include hardeners, strengtheners, chelating agents, emollients, colorants, perfumes, emulsifiers, and fillers. Optional components useful herein are disclosed in the following patent documents, all incorporated by reference herein in their entirety: U.S. Pat. No. 3,255,082, to Barton, issued June 7, 1966; U.S. Pat. No. 4,049,792, to Elsnau, issued Sept. 20, 1977; U.S. Pat. No. 4,137,306, to Rubino et al., issued Jan. 30, 1979; U.S. Pat. No. 4,279,658, to Hooper et al., issued July 14, 1981; and European Patent Specification No. 117,070, to May, published Aug. 29, 1984. Optional components for use in the present invention may also include non-water-soluble deodorant actives and/or antiperspirant actives.

The specific essential and optional materials to be included in specific stick compositions of the present invention, and their levels, are selected in order to produce a stick of desired hardness so as to maintain dimensional stability while depositing a suitable amount of active material on the skin during normal use. Hardness of sticks can be determined in a variety of methods, including American Society for Testing Materials (ASTM) Method D-5. This method involves the use of a needle or polished cone of particular weight and dimension, which is allowed to travel downward through the stick material for a predetermined period of time. The distance traveled by the needle or cone is a relative measure of the stick hardness. Utilizing Method D-5, with a penetration cone (Model H1310; sold by Humboldt Manufacturing Company) weighing 2.52 grams, and a Precision Model 14AN-8 Penetrometer (sold by GCA Corp.), the cosmetic sticks of the present invention preferably yield a penetration value of from about 5.0 to about 15.0 millimeters, more preferably from about 7.5 to about 12.5 millimeters, over a period of 5 seconds. These values represent an average penetration for sticks within a given production batch, since such penetration values may vary from stick to stick within the batch.

Another measure of the hardness of the preferred cosmetic sticks of the present invention is a break strength measurement. The break strength is determined using a Velmex Inc. Model B2509BJ (sold by Crown Tool & Supply Co.). In this instrument the force gauge is attached to a slide which allows the gauge to contact the test stick through a breaker bar at a speed of 3.3 inches per minute. The value recorded is the force gauge reading when the stick breaks. The cosmetic sticks of the present invention preferably have break strength within the range of from about 10 to about 30 pounds.

Methods for Malodor Prevention

The present invention also provides methods for treating or preventing malodor associated with human perspiration, especially underarm odor. These methods comprise applying to the skin of a human a safe and effective amount of a cosmetic stick composition of the present invention containing a deodorant active, antiperspirant active, or mixtures thereof. The term "a safe and effective amount", as used herein, is an amount which is effective in eliminating or substantially reducing the malodor associated with human perspiration, especially underarm odor, while being safe for human use at a reasonable risk/benefit ratio.

Methods for Manufacturing Cosmetic Stick Compositions

The present invention further relates to methods for manufacturing cosmetic stick compositions of the present invention. These methods comprise the steps of:
(a) dissolving at least one water-soluble active in an aqueous phase comprising the water component; followed by
(b) mixing this aqueous active solution with an organic phase comprising at least one of the components selected from dimethicone copolyol, volatile silicone oil, or mixtures thereof.

The aqueous phase may comprise some or all of the essential water component of the cosmetic stick to be formulated, preferably all of the water component. The organic phase may comprise some or all of at least one of the essential components selected from dimethicone copolyol, volatile silicone oil, or mixtures thereof; preferably all of both the dimethicone copolyol and the volatile silicone oil.

Most preferred is the method comprising:
(a) dissolving a water-soluble active (especially a bicarbonate salt) in the water component of the cosmetic stick to be formulated; followed by
(b) mixing this aqueous active solution with an organic phase comprising dimethicone copolyol, volatile silicone oil, propylene glycol, $C_2$–$C_4$ monohydric alcohol, solidifying agent, and coupling agent at a temperature between about 35° C. and about 100° C.

The following examples further describe and demonstrate embodiments within the scope of the present invention. The examples are given solely for the purpose of illustration and are not to be construed as limitations of the present invention as many variations thereof are possible without departing from the spirit and scope.

EXAMPLE I

Bicarbonate-Containing Deodorant Stick

A sodium bicarbonate-containing silicone deodorant stick of the present invention is prepared comprising the following ingredients:

| Components | Weight % |
| --- | --- |
| Distilled water | 23.0% |
| Dimethicone copolyol[1] | 15.0% |
| Cyclomethicone D-5[2] | 10.0% |
| Propylene glycol | 12.4% |

-continued

| Components | Weight % |
| --- | --- |
| PPG-3 myristyl ether[3] | 10.0% |
| PPG-10 cetyl ether[4] | 10.0% |
| SDA-40 alcohol[5] | 8.0% |
| Sodium stearate | 6.5% |
| Sodium bicarbonate | 2.0% |
| Fragrance | 1.3% |
| FD&C Blue #1 | 1.0% |
| FD&C Yellow #5 | 0.5% |
| Triclosan[6] | 0.3% |

[1]Dow Corning 3225C Silicone Fluid; sold by Dow Corning Corporation.
[2]SF-1202 Silicone Fluid; sold by General Electric.
[3]Procetyl 10; sold by Croda. This is a polypropylene glycol ether (average of 10 propylene glycol units per polymer) of cetyl alcohol.
[4]Witconol APM; sold by Witco Organics. This is a polypropylene glycol ether (average of 3 propylene glycol units per polymer) of myristyl alcohol.
[5]Denatured ethanol (200 proof); sold by Raper Alcohol.
[6]Irgasan DP-300; sold by Ciba-Geigy This deodorant stick composition is prepared on a 750 gram scale as follows. The reaction vessel is charged with the dimethicone copolyol, propylene glycol, PPG-3 myristyl ether, PPG-10 cetyl ether, cyclomethicone D-5, SDA-40 alcohol, sodium stearate, and the triclosan. This mixture is heated with vigorous stirring to 180° F. (82° C.). In the meantime, the sodium bicarbonate is heated in the water to 120° F. (49° C.). This aqueous bicarbonate solution is then added to the organic phase. The resulting mixture is cooled with stirring to about 135° F. (57° C.), and the fragrance and colors are then added. Following further cooling to 121°–122° F. (49° to 50° C.), the mixture is poured into canisters. The mixture solidifies upon cooling to give homogeneous gel type deodorant sticks.

This deodorant stick composition is applied to the underarm skin of a human to effectively prevent underarm odor resulting from perspiration. The composition during application to the skin has a dry feel, and does not feel greasy or gritty. The composition provides a clean and clear coat of deodorant protection.

EXAMPLES II–VI

Deodorant Stick Compositions

Gel type sodium bicarbonate-containing silicone deodorant sticks of the present invention also include the following compositions:

| Components | Weight % | | | | |
| --- | --- | --- | --- | --- | --- |
| | Ex. II | Ex. III | Ex. IV | Ex. V | Ex. VI |
| Distilled water | 23 | 23 | 23 | 23 | 35.27 |
| Dimethicone copolyol[1] | 15 | 15 | 15 | 15 | 11.80 |
| Cyclomethicone D-5[2] | 10 | 10 | 10 | 10 | 7.83 |
| Propylene glycol | 12.2 | 12.2 | 12.2 | 12.2 | 15.09 |
| PPG-3 myristyl ether[3] | 10 | — | 4 | 20 | 5.32 |
| PPG-10 cetyl ether[4] | 10 | 20 | 16 | — | 5.46 |
| SDA-40 alcohol[5] | 8 | 8 | 8 | 8 | 6.48 |
| Sodium stearate | 6.5 | 6.5 | 6.5 | 6.5 | 5.07 |
| Sodium bicarbonate | 2 | 2 | 2 | 2 | 5.45 |
| Fragrance | 1.5 | 1.5 | 1.5 | 1.5 | 1.09 |
| Color | 1.5 | 1.5 | 1.5 | 1.5 | 1.14 |
| Triclosan[6] | 0.3 | 0.3 | 0.3 | 0.3 | — |

[1]Dow Corning 3225C Silicone Fluid; sold by Dow Corning Corporation.
[2]SF-1202 Silicone Fluid; sold by General Electric.
[3]Procetyl 10; sold by Croda. This is a polypropylene glycol ether (average of 10 propylene glycol units per polymer) of cetyl alcohol.
[4]Witconol APM; sold by Witco Organics. This is a polypropylene glycol ether (average of 3 propylene glycol units per polymer) of myristyl alcohol.
[5]Denatured ethanol (200 proof); sold by Raper Alcohol.
[6]Irgasan DP-300; sold by Ciba-Geigy These compositions are prepared similar to the preparation of the stick composition described in Example I. These compositions provide very good underarm deodorant protection. The sticks deposit an effective amount of deodorant active as a clean and clear looking coating without feeling gritty or greasy during application.

EXAMPLE VII

Antiperspirant Cosmetic Stick

A chloracel-containing antiperspirant stick of the present invention is prepared as follows:

| Components | Weight % |
| --- | --- |
| Distilled water | 19.90 |
| Dimethicone copolyol[1] | 13.00 |
| Cyclomethicone D-5[2] | 8.60 |
| Propylene glycol | 10.50 |
| PPG-3 myristyl ether[3] | 8.60 |
| PPG-10 cetyl ether[4] | 8.60 |
| SDA-40 alcohol[5] | 6.90 |
| Sodium stearate | 5.60 |
| Chloracel[6] | 15.60 |
| Fragrance | 1.30 |
| Color | 1.40 |

[1]Dow Corning 3225C Silicone Fluid; sold by Dow Corning Corporation.
[2]SF-1202 Silicone Fluid; sold by General Electric.
[3]Procetyl 10; sold by Croda. This is a polypropylene glycol ether (average of 10 propylene glycol units per polymer) of cetyl alcohol.
[4]Witconol APM; sold by Witco Organics. This is a polypropylene glycol ether (average of 3 propylene glycol units per polymer) of myristyl alcohol.
[5]Denatured ethanol (200 proof); sold by Raper Alcohol.
[6]Sodium aluminum chlorohydroxy lactate sold by Reheis Chemical Company.

A 115.7 g batch of this chloracel-containing stick composition is prepared as follows. Chloracel (18.0 g) is dissolved in distilled water (23.00 g) at 120° F. (49° C.). The other components, minus the fragrance and color, are mixed together and heated to 180° F. (82° C.). The water/chloracel phase is then added to the total mixture. After allowing this mixture to cool, the fragrance and color are added at 134° F. (57° C.) and this mixture is then poured into cannisters at 130° F. (54° C.).

Use of this stick by applying a thin layer to the underarm area of a human provides antiperspirant activity from a cosmetically-acceptable stick.

What is claimed is:

1. A cosmetic stick composition comprising:
   (a) from about 0.1% to about 50% of at least one water-soluble active selected from the group consisting of deodorant actives, antiperspirant actives, and mixtures thereof;
   (b) from about 5% to about 25% of at least one dimethicone copolyol;
   (c) from about 1% to about 25% of at least one volatile silicone oil selected from the group consisting of cyclic and linear polydimethylsiloxanes containing from about 3 to about 9 silicon atoms;
   (d) from about 5% to about 20% of propylene glycol;
   (e) from about 1% to about 15% of at least one $C_2$–$C_4$ monohydric alcohol selected from the group consisting of ethanol, n-propanol, isopropanol, and mixtures thereof;
   (f) from about 10% to about 50% water;
   (g) from about 1% to about 25% of at least one solidifying agent; and
   (h) from about 1% to about 30% of at least one coupling agent selected from the group consisting of $C_6$–$C_{22}$ fatty alcohols, ethoxylated derivatives of $C_4$–$C_{22}$ fatty alcohols, propoxylated derivatives of $C_4$–$C_{22}$ fatty alcohols, and mixtures thereof, having an HLB value within the range of from about 5 to about 18.

2. A cosmetic stick composition according to claim 1 wherein:
   (a) the water-soluble active is a deodorant active in an amount from about 1% to about 10%;
   (b) the solidifying agent is a soap type gel forming agent; and
   (c) the coupling agent is selected from the group consisting of $C_6$–$C_{22}$ fatty alcohols, ethoxylated derivatives of $C_4$–$C_{22}$ fatty alcohols, propoxylated derivatives of $C_4$–$C_{22}$ fatty alcohols, and mixtures thereof, having an HLB value within the range of from about 5 to about 18.

3. A cosmetic stick composition according to claim 2 wherein:
   (a) the water-soluble active is selected from the group consisting of carbonate salts, bicarbonate salts, and mixtures thereof;
   (b) the volatile silicone oil is selected from the group consisting of cyclic and linear dimethylsiloxanes containing from about 3 to about 9 silicon atoms;
   (c) the monohydric alcohol is selected from the group consisting of ethanol, n-propanol, isopropanol, and mixtures thereof; and
   (d) the coupling agent is selected from the group consisting of polypropylene glycol ethers of $C_4$–$C_{22}$ fatty alcohols.

4. A cosmetic stick composition comprising:
   (a) from about 1% to about 10% of at least one bicarbonate salt;
   (b) from about 10% to about 20% of at least one dimethicone copolyol;
   (c) from about 5% to about 15% of at least one volatile silicone oil;
   (d) from about 5% to about 20% of propylene glycol;
   (e) from about 1% to about 15% of at least one $C_2$–$C_4$ monohydric alcohol;
   (f) from about 10% to about 40% of water;
   (g) from about 1% to about 15% of at least one soap type gel forming agent; and
   (h) from about 5% to about 25% of at least one coupling agent.

5. A cosmetic stick composition according to claim 4 wherein:
   (a) the bicarbonate salt is selected from the group consisting of alkali metal bicarbonate salts;
   (b) the monohydric alcohol is selected from the group consisting of ethanol, n-propanol, isopropanol, and mixtures thereof; and
   (c) the coupling agent is selected from the group consisting of $C_6$–$C_{22}$ fatty alcohols, ethoxylated derivatives of $C_4$–$C_{22}$ fatty alcohols, propoxylated derivatives of $C_4$–$C_{22}$ fatty alcohols, and mixtures thereof, having an HLB value within the range of from about 5 to about 18.

6. A cosmetic stick composition according to claim 5 wherein:
   (a) the volatile silicone oil is selected from the group consisting of cyclic and linear polydimethylsiloxanes containing from about 3 to about 9 silicon atoms; and
   (b) the coupling agent is selected from the group consisting of polypropylene glycol ethers of $C_4$–$C_{22}$ fatty alcohols.

7. A cosmetic stick composition according to claim 6 wherein:
   (a) the bicarbonate salt selected from the group consisting of sodium bicarbonate, potassium bicarbonate, and mixtures thereof; and
   (b) the monohydric alcohol is ethanol.

8. A cosmetic stick composition according to claim 7 comprising:
   (a) from about 1% to about 10% sodium bicarbonate;
   (b) from about 10% to about 20% of at least one dimethicone copolyol;
   (c) from about 5% to about 15% of a volatile silicone oil selected from the group consisting of cyclic and linear polydimethylsiloxanes containing from about 3 to about 9 silicon atoms;
   (d) from about 5% to about 20% propylene glycol;
   (e) from about 1% to about 15% ethanol;
   (f) from about 10% to about 40% water;
   (g) from about 3% to about 10% of at least one soap type gel forming agent; and
   (h) from about 5% to about 25% of at least one coupling agent selected from the group consisting of polypropylene glycol ethers of $C_4$–$C_{22}$ fatty alcohols having an HLB value within the range of from about 5 to about 18.

9. A cosmetic stick composition according to claim 8 wherein:
   (a) the soap type gel forming agent is sodium stearate; and
   (b) the coupling agent is selected from the group consisting of PPG-3 myristyl ether, PPG-10 cetyl ether, and mixtures thereof.

10. A cosmetic stick composition according to claim 9 wherein the coupling agent is a mixture of PPG-3 myristyl ether/PPG-10 cetyl ether in a weight ratio within the range of from about 19:1 to about 1:1.

11. A cosmetic stick composition comprising:
    (a) about 2% sodium bicarbonate;
    (b) about 15% dimethicone copolyol;
    (c) about 10% cyclomethicone D-5;
    (d) about 12.4% propylene glycol;
    (e) about 8% ethanol;
    (f) about 23% water;
    (g) about 6.5% sodium stearate;
    (h) about 10% PPG-3 myristyl ether;
    (i) about 10% PPG-10 cetyl ether; and
    (j) the remainder comprising at least one component selected from the group consisting of fragrance, coloring agents, triclosan, and mixtures thereof.

12. A method for manufacturing a cosmetic stick composition according to claim 1, said method comprising the steps of:
    (a) dissolving at least one water soluble active in an aqueous phase comprising the water component; followed by
    (b) mixing this aqueous active solution with an organic phase comprising at least one of the components selected from the group consisting of dimethicone copolyol, volatile silicone oil, and mixtures thereof.

13. A method for manufacturing a cosmetic stick composition according to claim 4, said method comprising the steps of:
    (a) dissolving the bicarbonate salt in the water component; followed by
    (b) mixing this aqueous bicarbonate solution with an organic phase comprising dimethicone copolyol, volatile silicone oil, propylene glycol, ethanol, soap type gel forming agent, and coupling agent at a temperature between about 35° C. and about 100° C.

14. A method for manufacturing a cosmetic stick composition according to claim 11, said method comprising the steps of:
 (a) dissolving the sodium bicarbonate in the water; followed by
 (b) mixing this aqueous bicarbonate solution with the dimethicone copolyol, propylene glycol, PPG-3 myristyl ether, PPG-10 cetyl ether, cyclomethicone D-5, ethanol, and sodium stearate at a temperature between about 35° C. and about 100° C.

15. A method for treating or preventing malodor associated with human perspiration, said method comprising applying to the skin of a human a safe and effective amount of a cosmetic stick composition according to claim 1.

16. A method for treating or preventing underarm odor associated with human perspiration, said method comprising applying to the skin of a human a safe and effective amount of a cosmetic stick composition according to claim 4.

17. A method for treating or preventing underarm odor associated with human perspiration, said method comprising applying to the skin of a human a safe and effective amount of a cosmetic stick composition according to claim 11.

* * * * *

UNITED STATES PATENT AND TRADEMARK OFFICE
CERTIFICATE OF CORRECTION

PATENT NO. : 4,822,602
DATED : April 18, 1989
INVENTOR(S) : ANTHONY D. SABATELLI It is certified that error appears in the above-identified patent and that said Letters Patent is hereby corrected as shown below:

In column 5, line 19 "1 to about 2 carbon atoms" should read
--1 to about 12 carbon atoms--

Signed and Sealed this

Third Day of October, 1989

Attest:

DONALD J. QUIGG

*Attesting Officer*   *Commissioner of Patents and Trademarks*